United States Patent
Penney et al.

(10) Patent No.: US 9,858,663 B2
(45) Date of Patent: Jan. 2, 2018

(54) METHOD AND SYSTEM FOR TOMOSYNTHESIS IMAGING

(71) Applicant: Cydar Limited, Cambridgeshire (GB)

(72) Inventors: Graeme Penney, London (GB); Tom Carrell, London (GB); Mazen Alhrishy, London (GB)

(73) Assignee: Cydar Limited, Barrington, Cambridgeshire (GB)

(*) Notice: Subject to any disclaimer, the term of this patent is extended or adjusted under 35 U.S.C. 154(b) by 0 days.

(21) Appl. No.: 14/908,774

(22) PCT Filed: Aug. 1, 2014

(86) PCT No.: PCT/GB2014/052366
§ 371 (c)(1),
(2) Date: Jan. 29, 2016

(87) PCT Pub. No.: WO2015/015219
PCT Pub. Date: Feb. 5, 2015

(65) Prior Publication Data
US 2016/0163045 A1  Jun. 9, 2016

(30) Foreign Application Priority Data
Aug. 1, 2013  (GB) .................................. 1313810.2

(51) Int. Cl.
*G06T 7/00* (2017.01)
*G06T 11/00* (2006.01)
(Continued)

(52) U.S. Cl.
CPC .............. *G06T 7/0012* (2013.01); *G06T 5/50* (2013.01); *G06T 11/003* (2013.01);
(Continued)

(58) Field of Classification Search
CPC ....... G06T 7/0012; G06T 5/50; G06T 11/003; G06T 11/006; G06T 15/20; G06T 2207/10081; G06T 2207/10088; G06T 2207/20224; G06T 2211/412; G06T 2211/428; G06T 2211/436; G06T 2207/10112; A61B 6/025
See application file for complete search history.

(56) References Cited

U.S. PATENT DOCUMENTS 5,734,739 A * 3/1998 Sheehan ............... G06T 7/0012
                                                            382/128
8,045,780 B2  10/2011 Boese et al.
(Continued)

OTHER PUBLICATIONS

Liu et al. "Generalized Tomosynthesis for Focusing on an Arbitrary Surface." IEEE Transactions on Medical Imaging, vol. 8, No. 2, Jun. 1989, pp. 168-172.*
(Continued)

*Primary Examiner* — Jon Chang
(74) *Attorney, Agent, or Firm* — Sterne, Kessler, Goldstein & Fox P.L.L.C.

(57) ABSTRACT

An image generation method is described, comprising obtaining a plurality of 2D images through an object to be imaged, obtaining a 3D image data set of the object to be imaged, and registering the 2D images with the 3D image data set. The method then further includes defining an image reconstruction plane internal to the object, being the plane of an image to be reconstructed from the plurality of 2D images. Then, for a pixel in the image reconstruction plane, corresponding pixel values from the plurality of 2D images are mapped thereto, and the mapped pixel values are combined into a single value to give a value for the pixel in the image reconstruction plane. Another aspect of the method provides for clutter removal from the image. In a medical imaging context this can provide for "de-boned" images, allowing soft tissue to be more clearly seen.

18 Claims, 13 Drawing Sheets

(51) Int. Cl.
*G06T 15/20* (2011.01)
*G06T 5/50* (2006.01)
*A61B 6/02* (2006.01)

(52) U.S. Cl.
CPC ............ G06T 11/006 (2013.01); G06T 15/20 (2013.01); *G06T 2207/10081* (2013.01); *G06T 2207/10088* (2013.01); *G06T 2207/20224* (2013.01); *G06T 2211/412* (2013.01); *G06T 2211/428* (2013.01); *G06T 2211/436* (2013.01)

(56) References Cited

U.S. PATENT DOCUMENTS

| 2007/0076928 A1* | 4/2007 | Claus | G06T 11/006 |
| | | | 382/128 |
| 2009/0274354 A1* | 11/2009 | Ng | A61B 6/025 |
| | | | 382/131 |
| 2016/0042537 A1* | 2/2016 | Ng | G06T 11/005 |
| | | | 382/131 |

OTHER PUBLICATIONS

Penney, et al. "An Image-Guided Surgery System to Aid Endovascular Treatment of Complex Aortic Aneurysms: Description and Initial Clinical Experience" Information Processing in Computer-Assisted Interventions, RH Taylor & G-Z Yang (Eds), Springer-Verlag, Berlin Heidelberg, pp. 13-24 (2011).

* cited by examiner

| | TI (a) | CI (b) | DTS (c) | DDTS (d) |
|---|---|---|---|---|
| PL1: CNR (Imp.) | 0.43 (-%) | 1.10 (156%) | 4.69 (990%) | 4.77 (1000%) |
| PL2: CNR (Imp.) | 0.25 (-%) | 0.28 (12%) | 3.67 (1308%) | 5.06 (1824%) |
| PL3: CNR (Imp.) | 0.56 (-%) | 0.63 (12%) | 4.50 (703%) | 4.61 (723%) |
| PL4: CNR (Imp.) | 0.64 (-%) | 1.33 (108%) | 6.37 (895%) | 6.25 (877%) |
| Average Imp. | - | 72% | 989% | 1133% |

METHOD AND SYSTEM FOR TOMOSYNTHESIS IMAGING

CROSS-REFERENCE TO RELATED APPLICATIONS

This application is a 371 National Stage entry of International Application No. PCT/GB2014/052366, filed Aug. 1, 2014, which claims benefit of GB 1313810.2, filed Aug. 1, 2013, both of which are incorporated herein by reference in their entirety.

TECHNICAL FIELD

The present invention relates to a method and system for tomosynthesis imaging, for example for intraoperative imaging of a human or animal body during a surgical procedure. Particular embodiments of the invention provide for tomosynthesis imaging wherein artefacts may be removed from the obtained image to provide an improved image, and/or where the imaging plane may be manipulated to provide a precise, in some cases non-planar or curved, imaging plane tailored to the specific imaged object and for the procedure being performed.

BACKGROUND TO THE INVENTION AND PRIOR ART

The fundamentals behind interventional fluoroscopy remain largely unchanged since its inception. Big advances have been made in detector sensitivity, however, clinicians still view 2D projective "shadow" images which simply integrate all information along the beam path. This often results in clinically relevant information being obscured by over or underlying anatomy.

Enhancement of blood vessels using iodinated contrast is routine, but must be used sparingly as contrast is nephrotoxic. In modern fluoroscopy suites 3D imaging is often available via semicircular C-arm rotation, i.e. cone beam CT (CBCT). However, the set-up time for CBCT (5_10 minutes) can cause a large interruption to clinical work-flow, especially if multiple acquisitions are required [11]. Set-up time includes: patient positioning to isocenter the area of interest, clearing the gantry's path of obstructions and preparing the contrast medium. In addition, the 3D nature of CBCT images requires some interaction from clinicians to scan through 2D sections to find the clinically relevant information. Repeated CBCT involves a significant radiation dose [2]. For these reasons, CBCT is not a natural interventional modality, and is unlikely to be used repeatedly during interventions to aid guidance.

Tomosynthesis was the first medical sectional modality, but was largely superseded by computed tomography after its invention in the 1970s. In the last decade, however, digital tomosynthesis (DTS) is being increasingly used for diagnosis of breast lesions and pulmonary nodules in the chest [3, 10] as it offers some of the tomographic benefits of CT but at substantially lower dose and shorter acquisition time [4]. Nevertheless, such diagnostic systems require dedicated equipment.

FIG. 1 illustrates how basic digital tomosynthesis systems operate. The top figure shows how a translation of an x-ray source with respect to a fluoroscopy screen (between positions A, B and C) produces three different fluoroscopy images (images A, B, and C) of the patient. The bottom figures then show how by shifting the images different amounts, and summing features, then different depths within the patient can be brought into focus. For example, by appropriate shifting an adding of the images A, B, and C either the sectional slice including the triangle feature or the sectional slice including the square feature may be imaged. However, it will also be seen how features in other slices either above or below the slice can cause image artefacts, as it can be seen in the respective resultant images that artefacts are causes by the other features (i.e. the square in the case of the section for the triangle, and vice versa).

Nearly all DTS systems have been proposed for diagnostic use, however, recently a 3D DTS prototype system, based on a mobile isocentric C-arm, has been proposed for intraoperative guidance of head and neck surgery [1, 2, 9]. The limited DTS arc (e.g. 20° to 90°) enabled a short acquisition time and low radiation dose causing minimal interruption to surgical work-flow [2]. However, apart from being modified for intraoperative use, the prototype still employs the same technique as diagnostic DTS systems and suffers from the same drawbacks.

In addition to the above, registration of preoperative 3D data to 2D intraoperative fluoroscopy data has been widely proposed for a number of clinical applications. Systems for radiosurgery and neurosurgery are in widespread clinical use. These systems allow overlay of preoperative data onto interventional images or allow additional information from a preoperative Computerised Tomography (CT) scan (e.g. a radiotherapy plan) to be accurately aligned to the patient.

In more detail, prior to an operation a patient is typically subjected to a CT scan of the body area where the surgery will take place. This results in a three-dimensional image of the scanned body area. However, during surgery real time 2D fluoroscopy images are obtained of the same area, using for example a C-arm type fluoroscopy machine. However, a 2D fluoroscopy image may be insufficient to allow a surgeon to determine the precise position within the body of surgical instruments or surgical implants, particularly during catheter based MIS procedures.

In order to address the drawbacks of the 2D images, it is known to augment the 2D real time image with the 3D pre-obtained image, obtained, for example from a CT scan. The problem then arises of ensuring accurate registration of the 3D image with the 2D image i.e. ensuring that the 2D image is aligned with the correct parts of the 3D image. As is known already in the art, CT position and orientation is usually defined by six rigid body parameters, being three translations X, Y, and Z, and three rotations $\theta x$, $\theta y$, and $\theta z$. These can be divided into parameters which define movements parallel to the plane of the fluoroscopy image (in plane parameters $\theta x$, Y, and Z), and parameters which define movements a component of which is normal to the fluoroscopy plane (out-of-plane parameters $\theta y$, and $\theta z$, and X). The registration problem is then one of how to manipulate these parameters such that the 3D data volume becomes aligned with the 2D image such that the surgeon can have some confidence in the registration achieved.

Various registration techniques are known in the art. Specifically, in Penney et al "An Image-Guided Surgery System to Aid Endovascular Treatment of Complex Aortic Aneurysms: Description and Initial Clinical Experience", IPCAI 2011, LNCS 6689, pp. 13-24 the present inventors describe an intensity based registration technique which requires a starting position to be chosen by relying on visual inspection and identification of a vertebra in the fluoroscopy image.

SUMMARY OF THE INVENTION

Embodiments of the invention build on the above to provide a new digital tomosynthesis (DTS) technique which makes use of the known 2D to 3D registration techniques to allow DTS slices to be obtained using a standard fluoroscopy system. In particular, embodiments of the invention use digital tomosynthesis (DTS) as an interventional modality which allows repeated acquisitions and results in minimal interruption to standard clinical workflow. Moreover, DTS slices can be produced in embodiments of the invention with a standard fluoroscopy system; and patient-anatomy-specific DTS slices can be automatically produced to display the most clinically relevant information. The main drawback of current DTS is the presence of back-ground "clutter" from high contrast features outside the slice of interest. Embodiments of the invention also propose a method which can automatically remove clutter from bony anatomy.

From one aspect there is further provided an image generation method, comprising obtaining a plurality of 2D images through an object to be imaged, obtaining a 3D image data set of the object to be imaged, and registering the 2D images with the 3D image data set, if required. If the 2D images are already registered with the 3D image data set, for example by accurate relative placement of the object for both 2D and 3D imaging, then no such registration is required. The method then further includes defining an object specific image reconstruction plane internal to the 3D image data, being the plane of an image to be reconstructed from the plurality of 2D images. Then, for a pixel in the image reconstruction plane, corresponding pixel values from the plurality of 2D images are mapped thereto, and the mapped pixel values are combined into a single value to give a value for the pixel in the image reconstruction plane.

Another aspect of the invention provides a tomographic imaging method including obtaining a plurality of images through a subject to be imaged from a respective plurality of angles. An image reconstruction plane is then defined at which a reconstructed image is to be generated using information from the plurality of images. The reconstruction plane may be any of: curved, angled, discontinuous, multi-planar, or any combination thereof. In some embodiments the image reconstruction plane is defined within a 3D image data set of the object or subject to be imaged. Once the reconstruction plane has been defined, a reconstructed image is then generated at the image reconstruction plane, the image being generated in dependence on image data from one or more of the plurality of images.

A further aspect of the invention provides an image generation system, comprising an image processor. The image processor is arranged to register, if required, a plurality of 2D images through an object to be imaged with a 3D image data set of the object to be imaged. If the 2D images and the 3D images are already in registration, then no such step is needed. The image processor then defines an image reconstruction plane inside the 3D image data set, being the plane of an image to be reconstructed from the plurality of 2D images, and then, for a pixel in the image reconstruction plane, maps corresponding pixel values from the plurality of 2D images thereto, and combines the mapped pixel values into a single value to give a value for the pixel in the image reconstruction plane.

In embodiments of the invention the following example image reconstruction planes may be obtained. By a curved plane we mean a plane that exhibits a curved surface i.e. it is not simply planar, whether horizontal, angled or otherwise. By an angled plane we mean a plane that is not simply a horizontal section through the object essentially normal to the imaging axis of the imaging device, but instead, is arranged at an angle through the object. Such a plane would typically intersect the imaging axis of the imaging device at an acute or obtuse angle. By a discontinuous plane we mean a plane that exhibits one or more discontinuities, such as having one or more angled corners or edges, for example arising from the intersection of two or more planes, or by having areas missing therefrom. By multi-planar we mean that the image generation plane is formed from two or more spatially separate planes, which themselves may be curved, planar, angled, discontinuous, or any combination thereof. With all of the above in embodiments of the invention the image generation plane is not simply a single substantially horizontal planar slice through the object at a certain depth therein, arranged substantially normal to the imaging axis of the imaging sensor, as in the prior art. In addition, in most embodiments of the invention the image reconstruction planes are defined in the 3D data set, which is in registration with the 2D images that are captured.

Further aspects and features of the invention will be apparent from the appended claims.

BRIEF DESCRIPTION OF THE DRAWINGS

Further features and advantages of the present invention will become apparent from the following description of an embodiment thereof, presented by way of example only, and by reference to the drawings, wherein like reference numerals refer to like parts, and wherein.

DESCRIPTION OF THE EMBODIMENTS

The embodiments to be described provide for digital tomosynthesis which allows for the tomosynthesis image to be defined according to any desirable target image plane, including curved planes, angled planes, or composite planes comprising a plurality of planar or curved planes. The plurality of planes may be intersecting to provide a resultant target image plane, or the multiple planes may be at different positions (i.e. non-intersecting) if relevant clinical feature are present at such different positions. This has significant advantages in the surgical context as it allows a target image plane to be defined which can follow an anatomical feature. For example, a target image plane that follows the curve of the aorta can be defined, so that the resulting tomosynthesis image images the entire aorta along its length in a single image. Typically, in most embodiments the target image plane would be defined in a 3D image data set that has been pre-obtained of the subject or object to be imaged.

In addition, in some embodiments image artefacts can also be conveniently removed from the image. As described previously, tomosynthesis images often contain unwanted artefacts, for example from features in other slices, or from unwanted features in the desired image slice of interest. Some embodiments of the invention also provide techniques which allow for image artefacts to be removed. For example, in the surgical context hard or dense structures such as bone may be removed from the images using appropriate image processing to be described, to allow the soft tissue to be more clearly seen.

Specific embodiments of the invention will now be described. The specific embodiments provide an image guided surgical system that is able to receive fluoroscopy images from a fluoroscopy set and to produce reconstructed DTS images along any desired image plane, as described above.

Figure 1:
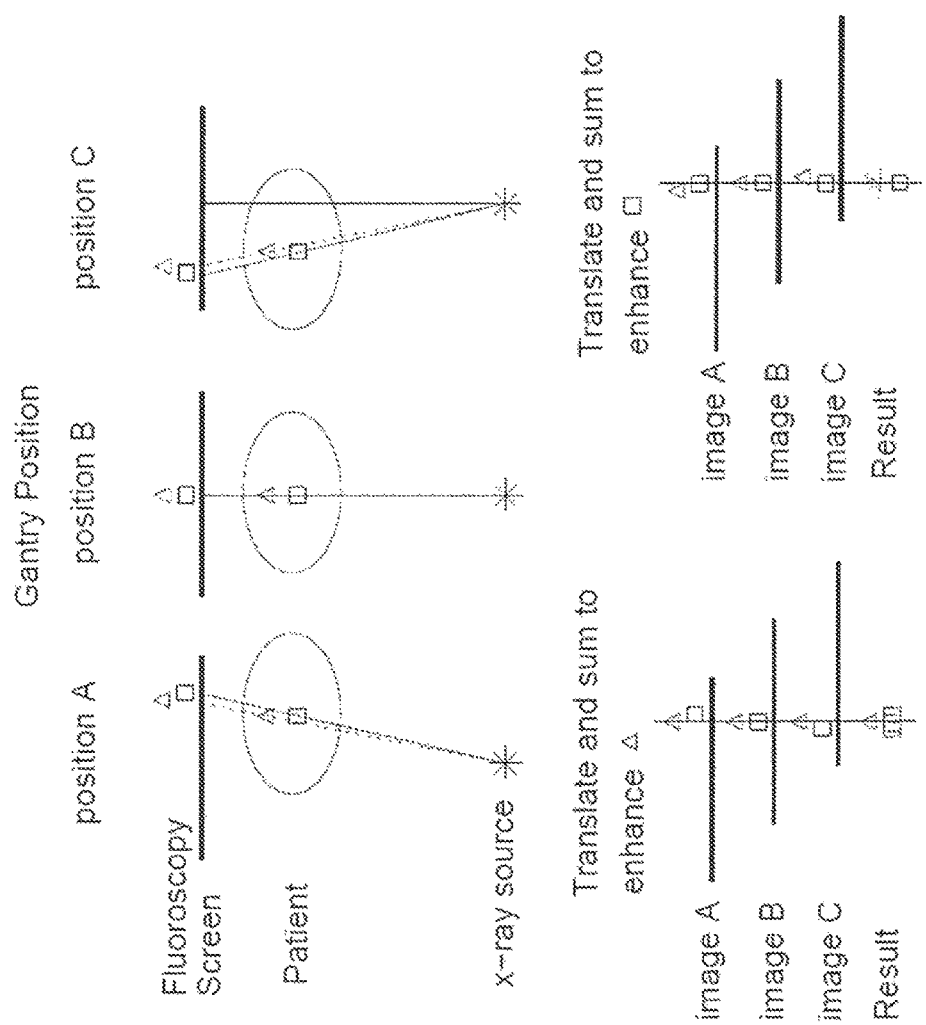
FIG. 1 is a diagram illustrating how standard digital tomosynthesis operates.
Figure 2:
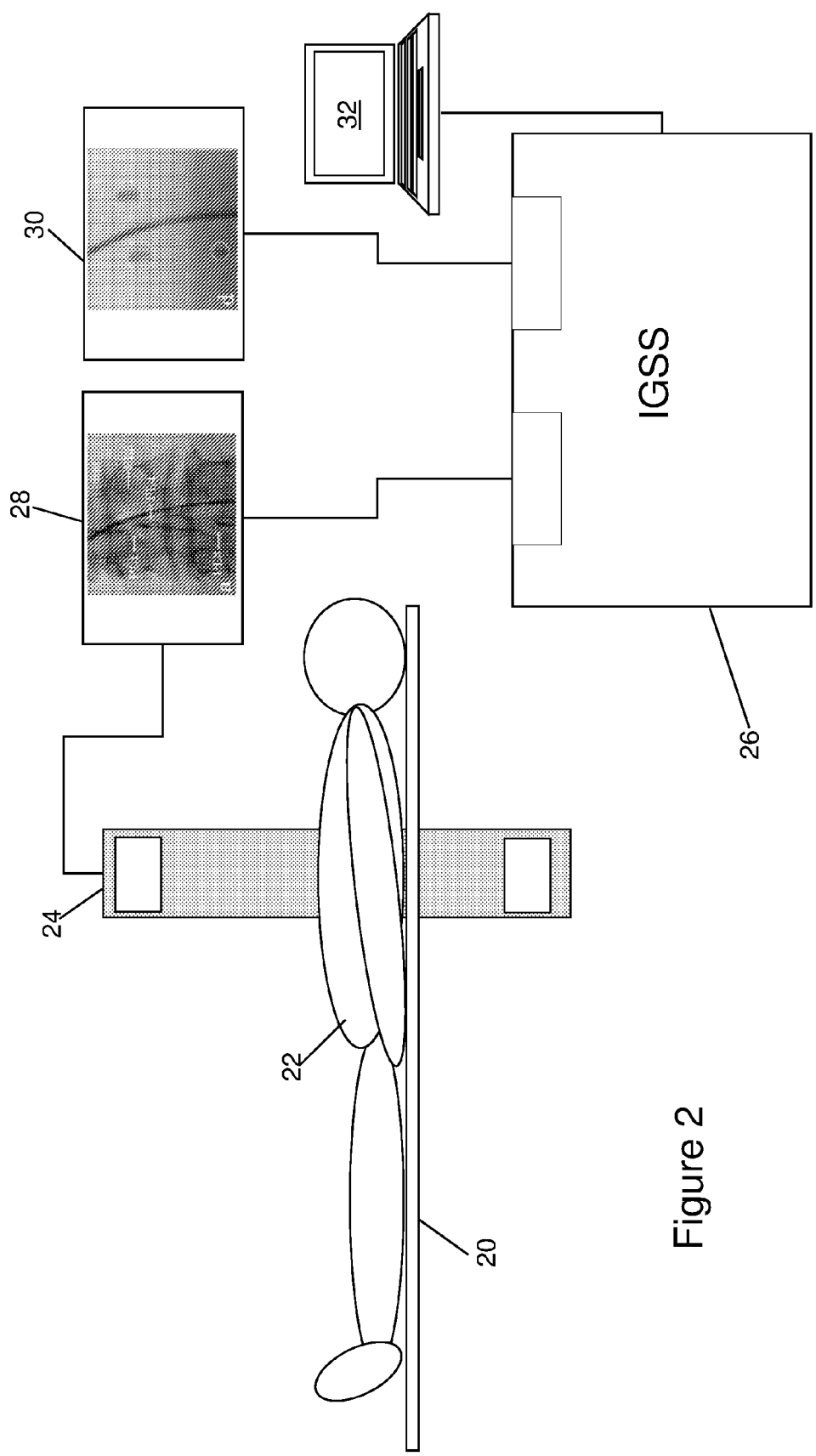
FIG. 2 is a diagram of an image guided surgical system according to an embodiment of the invention.

FIG. 2 shows in schematic form a typical fluoroscopy set and table. Operating table 20 is provided with a C-arm 24 on opposite sides of which are an X-ray source and detector. The X-ray images from the C-arm are displayed on X-ray display 28. The patient lies on the table between the source and detector. A computer based image guided surgical system 26 receives the x-ray images and shows on display 28 a target image from the fluoroscopy set and generates a reconstructed digital tomosynthesis (DTS) image in accordance with embodiments of the invention as shown on display 30. In this case, the image on display 30 is a deboned DTS image, the generation of which will also be described. The IGSS 26 is controlled via user input device 32, such as a keyboard or the like.

Figure 14:
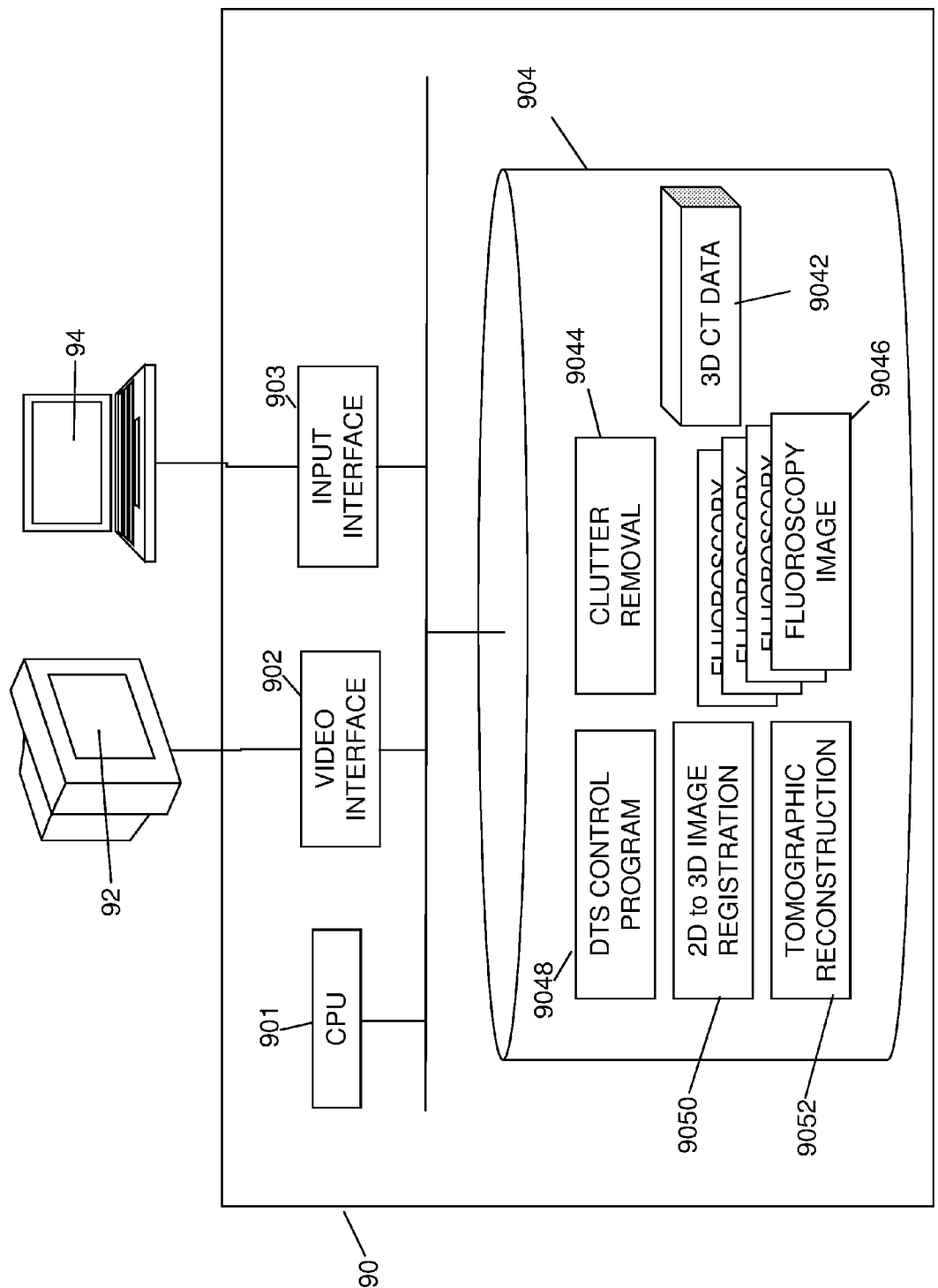
FIG. 14 is a block diagram of an embodiment of the invention.

FIG. 14 shows a general purpose computer system 90 forming part of the image guided surgical system 26, and having an output display 92 and user input features such as a keyboard 94 to allow control thereof. The computer comprises CPU 901, video interface 902 to control the display 92, and input interface 903 to receive user input from keyboard (or other input device) 94. Also provided is data storage medium 904, such as hard disk, solid state storage, or the like, upon which control programs and other data may be stored.

The data storage medium 904 has stored thereon a digital tomosynthesis control program 9048, that retains overall control of the computer 90 during the following procedures described below. Also stored thereon is a 2D to 3D image registration program 9050 that acts under the control of the control program to register 2D images obtained from a fluoroscopy set with a 3D image data set such as a CT or MRI data set previously obtained. Tomographic reconstruction program 9052 is also stored, and which is used to generate images along any desired target image plane in the data set for output as image 30, as described later. The input to the tomographic image generation program is 3D data 9042, obtained, for example, from a CT scan or the like. Also input are a plurality of fluoroscopy images 9046 obtained from a sweep of the fluoroscopy set C arm over the patient, as will be described. A clutter removal program 9044 is also provided, which acts under the control of the DTS control program 9048 to remove unwanted artefacts from the obtained fluoroscopy images, such as hard or bony features, again as will be described further later.

DTS slice reconstruction requires a set of 2D intraoperative images to be acquired from a limited range of view directions (e.g. ±20°). These are reconstructed into a sectional slice, commonly using the shift and add method described previously, which combines the fluoroscopy images so structures in the reconstruction plane line-up, and so appear in-focus, while structures outside the reconstruction plane are not aligned, and so are blurred-out.

In order to reconstruct a DTS slice, the following is required:
1. Relative view positions of input 2D images.
2. Reconstruction plane position with respect to the imaging device.

Standard diagnostic DTS obtains relative view positions using mechanical tracking. This requires a calibration process, and calibration errors can result in artefacts and reduced image quality [7].

For standard diagnostic DTS, a number of slices are reconstructed on planes defined with respect to the imaging device. Prior to reconstruction it is not possible to define a reconstruction plane to image specific regions of the patient's anatomy. DTS attempts to blur-out all structures outside the reconstruction plane, but because of the limited data acquisition, clutter from high contrast structures above and below the reconstruction plane remain. A number of methods have been proposed to reduce the effect of clutter [5], but this remains one of the main problems of DTS [6].

The DTS methods of embodiments of the invention described herein use an established intensity-based 2D/3D registration algorithm, as described in Penney, G., Varnavas, A., Dastur, N., Carrell, T.: *An Image-Guided Surgery System to Aid Endovascular Treatment of Complex Aortic Aneurysms: Description and Initial Clinical Experience*. IPCAI, vol. 6689, pp. 13-24 (2011), and elaborated on in Varnavas et al *Increasing the Automation of a 2D to 3D Registration System* IEEE transactions on Medical Imaging Vol 32 No. 2 Feb. 2013, and Varnavas et al, *Fully Automated Initialisation of 2D to 3D Image Registration* 2013 IEEE 10th International Symposium on Biomedical Imaging, San Francisco, Calif., Apr. 7-11 2013. In particular, as will be described, the embodiments use the 2D-3D registration techniques previously described to facilitate improved DTS reconstruction using standard hardware, on patient-anatomy-specific planes and with reduced clutter.

Figure 3:
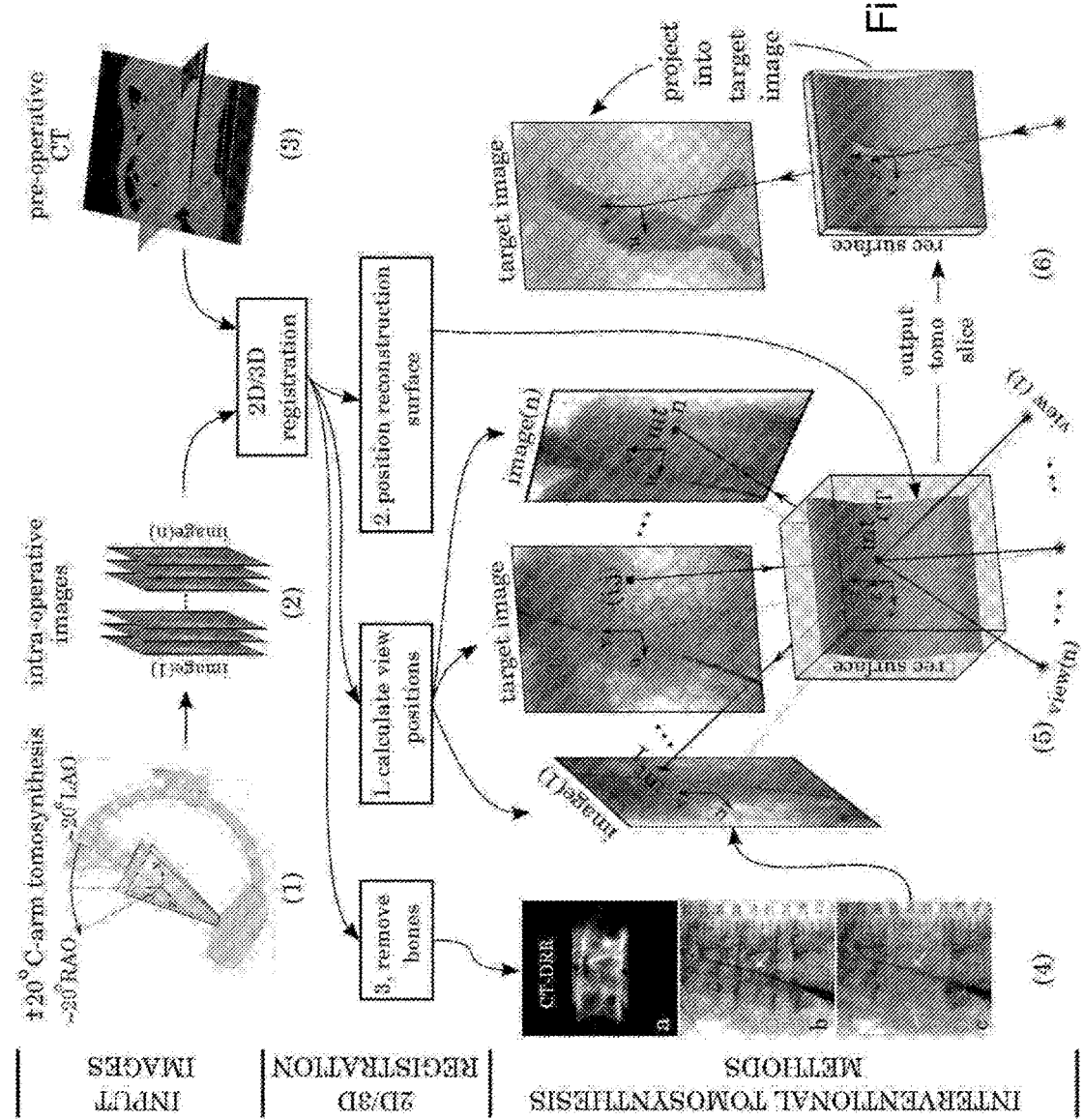
FIG. 3 is a diagram illustrating some of the procedures involved in embodiments of the invention.

FIG. 3 shows an overview of the entire process. This begins at the top with the input images, a C-arm sweep (1) to produce a set (of size n) of intraoperative fluoroscopy images (2) and a preoperative CT scan (3). These images are input into the 2D-3D registration algorithm which calculates the 2D-3D transformation Pi between the CT scan and each of the n fluoroscopy images. This registration process provides us with the necessary information to carry out DTS and enables us to greatly reduce clutter from bone as described below:
1. The transformations Pi enables relative view positions of input 2D images to be determined.
2. A patient-anatomy-specific plane can be preoperatively defined in the CT image. The transformations Pi can position this plane with respect to the fluoroscopy images, enabling reconstruction to occur on a patient-anatomy-specific plane.

3. Removing bones to greatly reduce clutter. After 2D-3D registration bony detail from the CT scan (in the form of a digitally reconstructed radiograph (DRR) as shown in FIG. 3.4.*a*, and in FIG. 9(*a*)) can be subtracted from the fluoroscopy image (FIG. 3.2.*b* and FIG. 9(*b*)) to give a "deboned" image (FIG. 3.2.*c* and FIG. 9(*c*)). Note how only the bone is removed leaving the interventional instruments and soft tissue details. This deboning process is carried out on each fluoroscopy image prior to reconstruction to greatly reduce clutter from high contrast bony features. Further details are given later.

Figure 7:
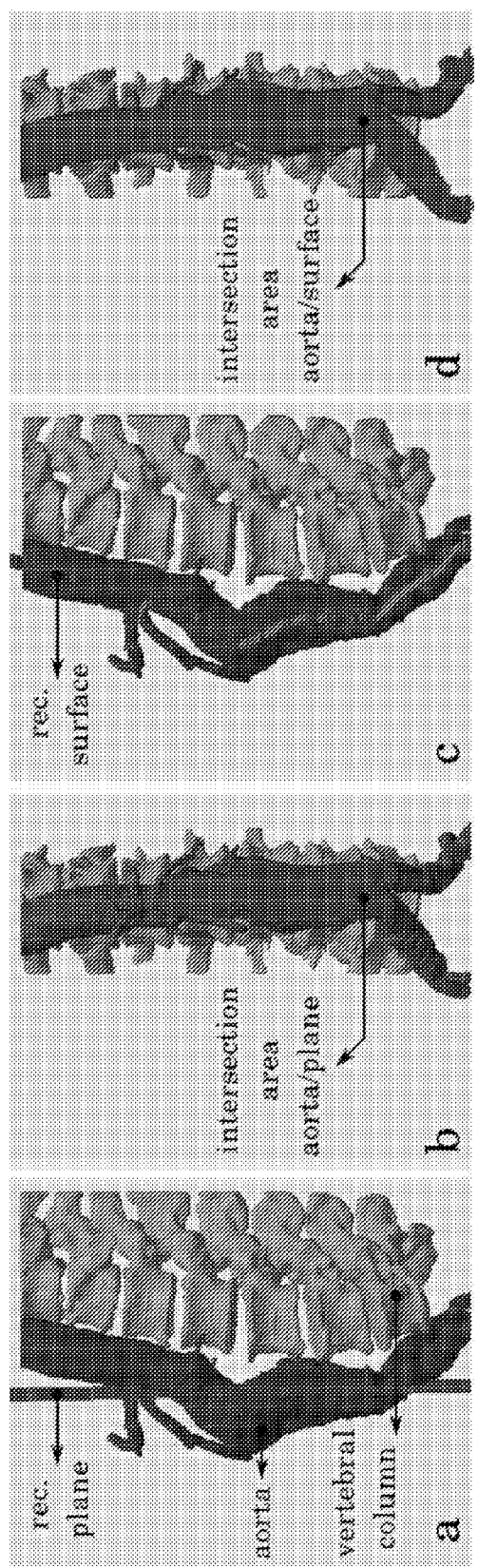
FIG. 7 (a) to (d) is a series of drawings illustrating the location of a reconstruction image plane that may be generated by embodiments of the invention—in this example the reconstruction plane has been defined in the 3D data set to follow the centreline of the imaged aorta.

In addition in embodiments of the invention we propose the use of curved patient-anatomy-specific reconstruction surfaces. It is rare that clinical structures lie on flat planes. Our aim in interventional tomosynthesis is to produce images with enhanced clinically relevant structures. As shown in FIG. 7 if the clinical structure of interest is the aorta then only approximately half of its length could be included in a flat reconstruction plane (see FIG. 7 (*a,b*)), whereas the use of a curved surface allows reconstruction of the entire length of the aorta (see FIG. 7 (*c,d*)). Because we register the 3D data set to the 2D fluoroscopy images we are able to automatically use a preoperatively defined reconstruction slice produced within the 3D data set. Such a slice can be defined to follow the clinically relevant structures within the 3D data set.

Returning to FIG. 3, the tomosynthesis process is shown in (5). Here, the information from the fluoroscopy images (after bone removal) is back projected onto the patient-anatomy-specific reconstruction surface using the transformation matrices Pi. The intensity values from each fluoroscopy image are summed to produce a curved patient-anatomy-specific tomosynthesis slice. In order to allow effective use of this new information, the reconstructed slice is then projected into the target image being used to guide the operation (6), thereby automatically producing an enhanced fluoroscopy image, showing additional information on the clinical features of interest, in a view familiar to clinicians.

Further details relating to the production of the image on any desired patient-anatomy-specific tomosynthesis slice will now be given with respect to FIGS. 4 to 7.

Figure 4:
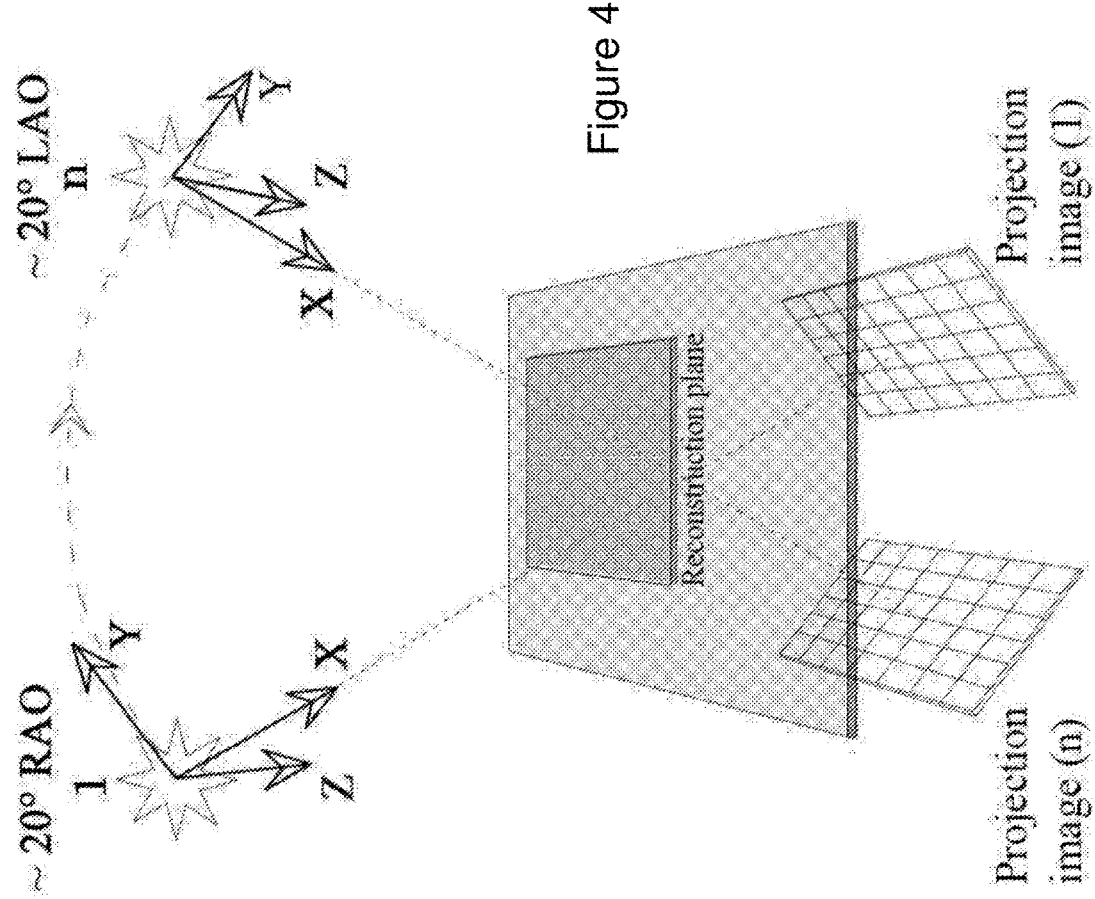
FIG. 4 is a diagram illustrating how the reconstruction plane position can relate to the acquired projection images.

FIG. 4 shows the main requirements to reconstruct a DTS slice. These are:

Relative view positions of input projection images.
Definition of the reconstruction plane position.

The relative positions of the n input projection images are usually achieved using dedicated machines with accurate mechanical tracking of the fluoroscopy gantry after a calibration process. For standard diagnostic DTS, a number of slices are reconstructed on planes defined with respect to the imaging device. Therefore, prior to reconstruction it is not possible to define a reconstruction plane to image specific regions of the patient's anatomy.

Figure 5:
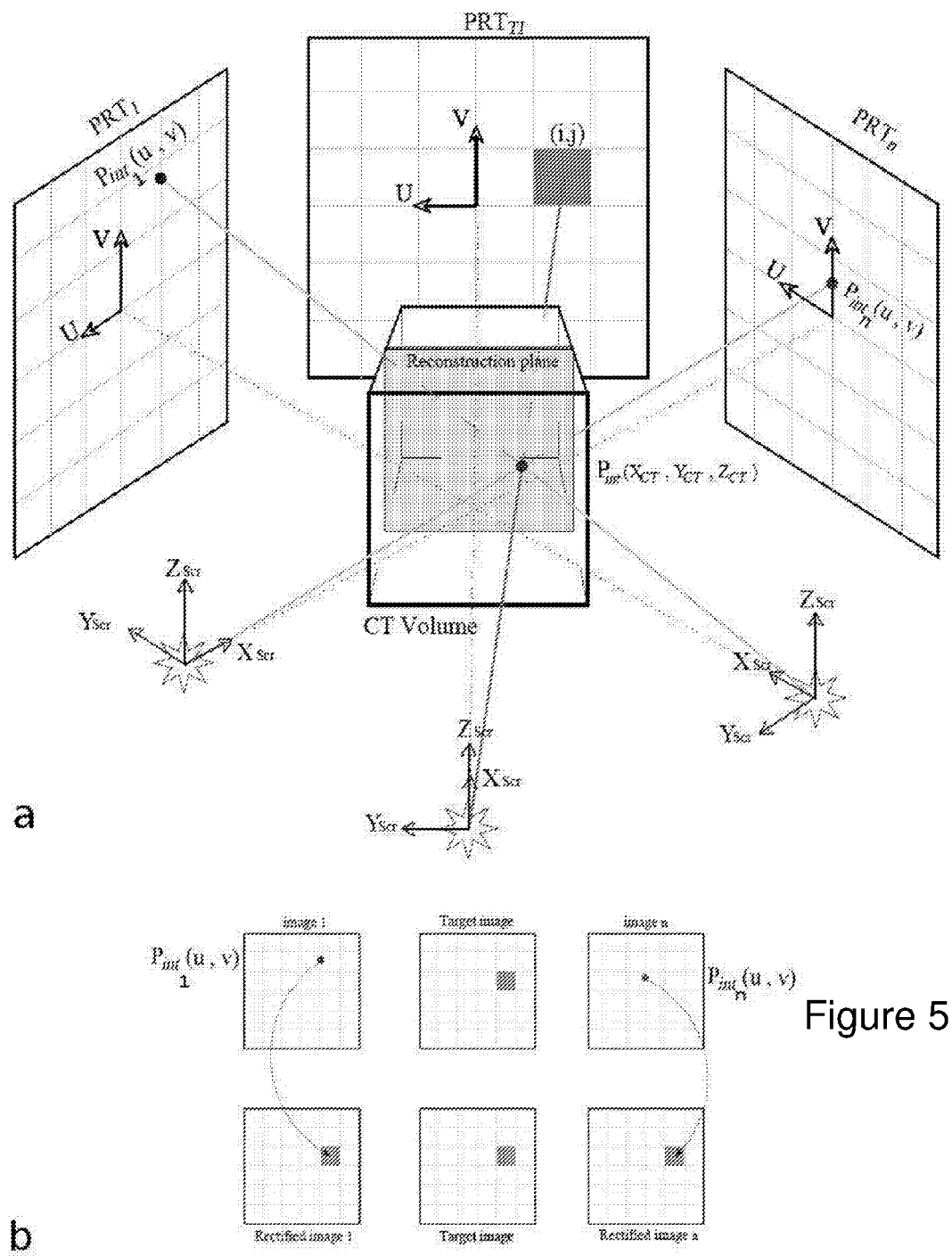
FIG. 5 is a diagram illustrating how a tomosynthesis image can be produced on a reconstruction image plane defined within the preoperative image. This is achieved via back and forward projection in an embodiment of the invention.

In embodiments of the invention, however, we are able to define a reconstruction plane of our choosing, which may be planar or curved, as desired, for example to image whole anatomical features along their length. In most embodiments, and particularly the medical imaging embodiments, the reconstruction plane is defined in the 3D image data set, so as to follow a particular anatomical feature. FIG. 5 illustrates this in more detail, and the method involves the following:

1. Segmenting a desired reconstruction surface from the preoperative CT. The surface should be chosen to contain structures of clinical interest to be enhanced. For example, a reconstruction surface or image plane which bisects the aorta along its length could be chosen.

2. Selecting a target image (TI) from the intraoperative fluoroscopy images. The image should be the fluoroscopy view which the clinicians wish to use to guide their instruments.

3. Using 2D/3D registration as described previously. This obtains relative view positions for the fluoroscopy images, Pi, i=1, . . . , n, and allows deboning prior to reconstruction. Deboning is optional, and further details thereof will be given later.

4. Back projecting rays from the target image pixels (using P(TI)) and calculating the 3D positions (in the CT coordinate system) where they intercept the reconstruction surface. These positions are saved along with the location of the pixel the ray was projected from.

5. Projecting rays from the 3D interception positions to each of the other fluoroscopy images in turn using the projection matrices Pi. The intensity at the 2D intercept position is mapped back to the target image pixel associated with the 3D intercept position. This process is known as image rectification according to a target image view and will be denoted as:

$$I_i' = Rec(I_i, P_i, P_{TI}, S)$$

where $I_i'$ is the rectified version of the ith fluoroscopy image Ii and S is the reconstruction surface.

6. Producing the tomosynthesis slice (R) by averaging all rectified images, i.e.

$$R = \frac{1}{n}\sum_{i=1}^{n} I_i'.$$

Hence, in FIG. 5(*a*) the relative view positions for ray projection are used: a ray is back projected from the target image (e.g. from position (I,j)) to the CT segmented reconstruction surface. The 3D intercept position P=(Xct, Yct, Zct) is then projected into each fluoroscopy image, e.g. PintI(u,v) is position in the 1st image calculated using P1. The intensity at PintI(u, v) is then mapped to position (i, j) in the rectified version of the first image, as shown in FIG. 5 (*b*).

Figure 6:
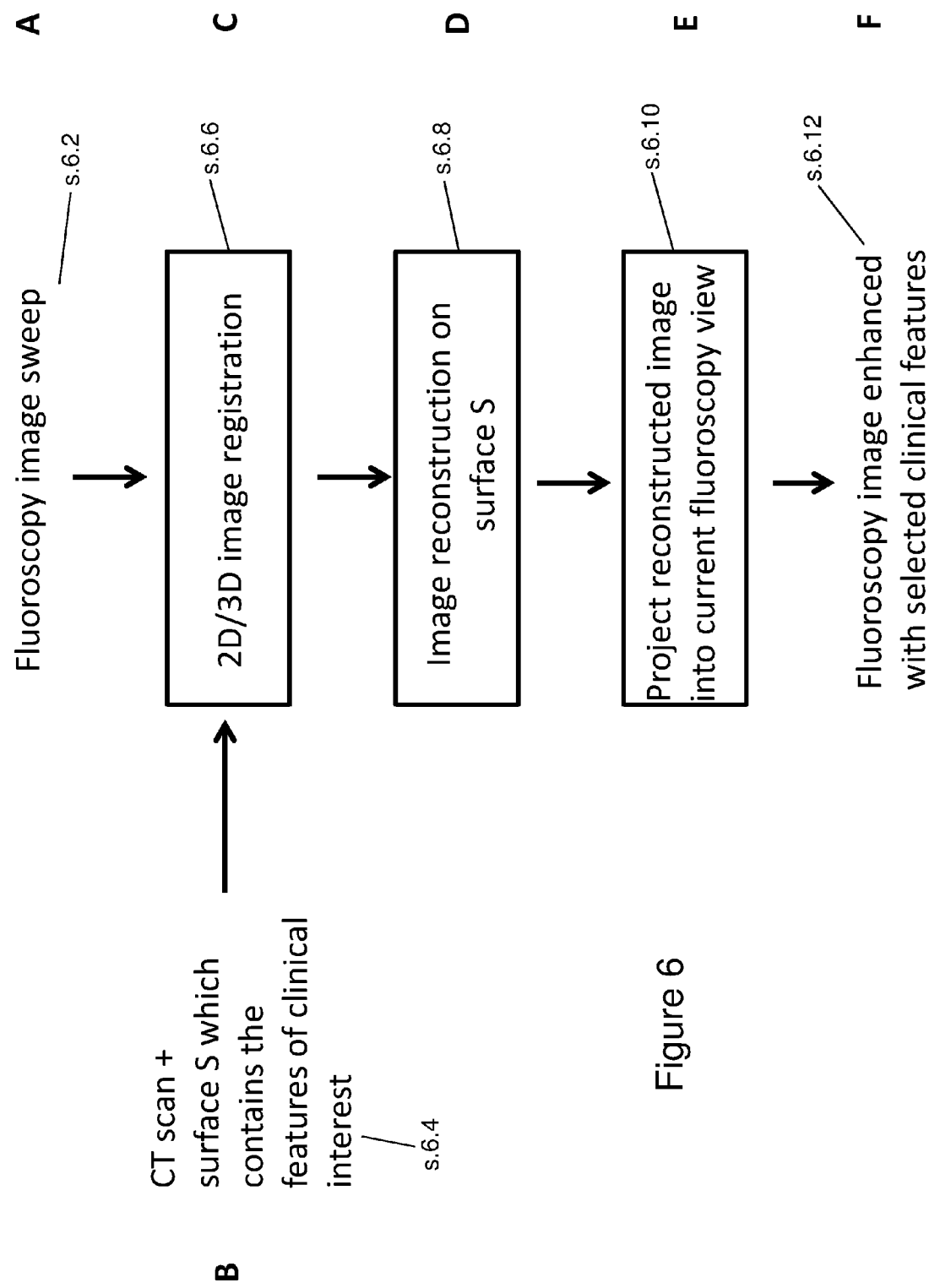
FIG. 6 is a flow diagram of an embodiment of the invention.

FIG. 6 is a flow diagram explaining the process of reconstructing along any desired plane further. Firstly at s.6.2 (A), a set of intraoperative fluoroscopy images from a range of views e.g. sweep from 20 deg RAO to 20 deg LAO is input. Then, at s.6.4 (B), the preoperative CT scan is input and the surface, S, to be reconstructed (which contains features of clinical interest) is defined. As mentioned previously, this surface does not need to be a flat plane, and may be determined either manually, automatically or semi-automatically depending on application. For example if a clinician wishes to enhance the aorta a surface could be generated which goes through the aorta midline and is parallel to a medial-lateral axis, as previously described. Other planes following other physiological features may of course be defined.

At s.6.6 (C) the preoperative CT scan is then registered to each of the fluoroscopy images using 2D-3D image registration. This enables the position of the surface, S, to be reconstructed to be determined in the fluoroscopy gantry coordinate system. A different relative position will be determined for each fluoroscopy image. As noted, the 2D-3D image registration procedures used are preferably those described in our previous papers, ibid.

At s.6.8 (D) image reconstruction is carried out using the fluoroscopy images to reconstruct a sectional image at position of surface S. Then, at s.6.10 (E) the sectional image is projected into the current fluoroscopy field of view. If the current field of view is one of the original fluoroscopy sweep images, then the registration calculated in step C can be used. Otherwise a separate registration will need to be carried out.

Finally, at s.6.12 (F) the output image is displayed on the screen 30. The output image is the current fluoroscopy image which has been enhanced with the clinical features present in the reconstructed sectional image at position of surface S that was defined in the 3D data set.

FIGS. 10c and 11c shows the results of the above, for an example where the image reconstruction surface follows the line of the aorta, as illustrated in FIGS. 7c and 7d. FIG. 7 also shows coverage obtained if a flat reconstruction plane is used. In particular, FIGS. 7(a) and 7(c) are saggital views showing: i) (FIG. 7(a)) a conventional flat reconstruction plane intersecting the aorta; and ii) (FIG. 7(c)) a curved reconstruction surface along the aortic centreline in accordance with the embodiment. FIGS. 7(b) and 7(c) then show anterior views showing: i) (FIG. 7(b)) that the flat plane of FIG. 7(a) only intersects with roughly half of aorta; whereas (FIG. 7(d)) the curved plane provided by embodiments of the invention can intersect (and therefore can reconstruct) the entire aorta.

With the above, therefore, digital tomosynthesis can be performed using an IGSS which is able to reconstruct an image from any desired image plane defined on the preoperative image, including curved planes, or discontinuous planes. This is possible because of the accurate 2D to 3D registration between the fluoroscopy images and the 3D data set, which means that it is possible to define a desired reconstruction plane in the 3D CT data set into which a ray from a target image to be displayed is back projected. The intersection of the back projected ray with the desired reconstruction image plane at a target pixel position is then forward projected into each of the 2D fluoroscopy images, and the intensities at the multiples 2D intercept positions thus obtained (i.e. one intercept position from each fluoroscopy image) are mapped back to the target image pixel. The value of the target image pixel in the reconstruction plane is then found by averaging the mapped back values from each of the fluoroscopy images.

Figure 9:
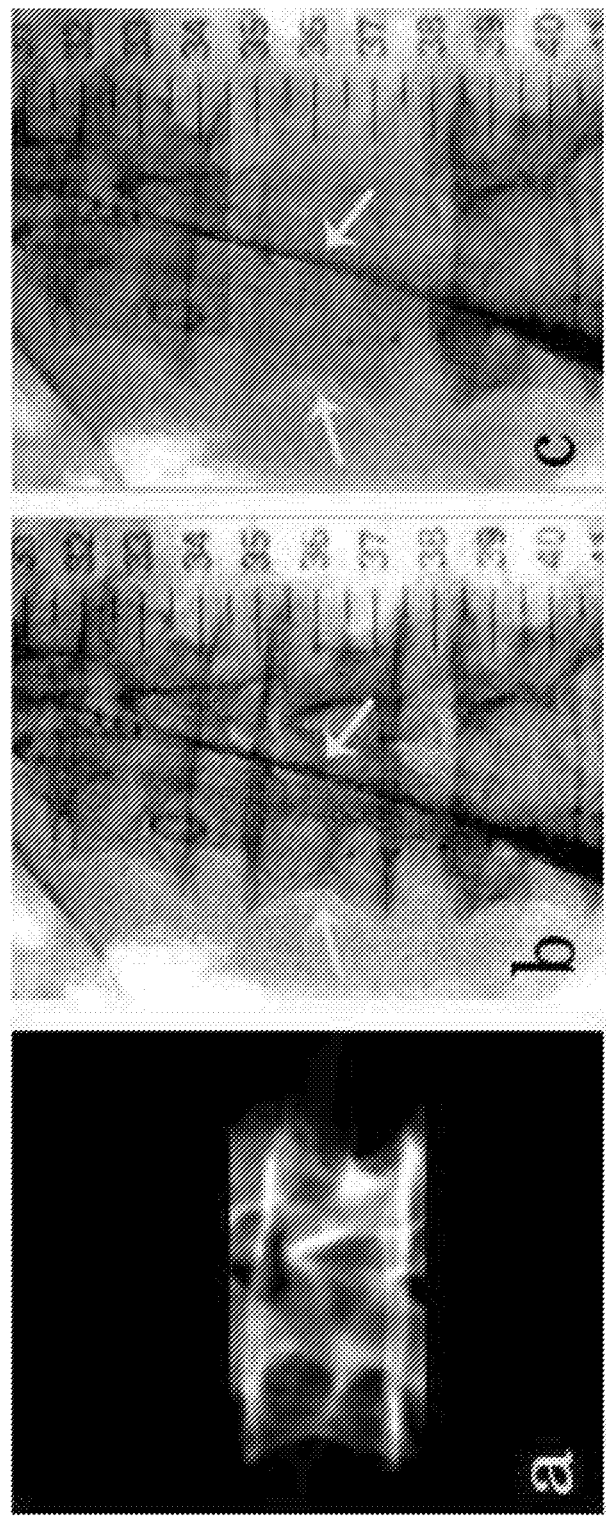
FIG. 9(a) is a DRR image and FIGS. 9(b) and (c) are fluoroscopy images obtained by embodiments of the invention.

In addition to the above, embodiments of the invention also allow for the removal of high contrast structures or artefacts in the image, either as an addition to the ability to be able to image any desired reconstruction plane, or independently thereof. In particular, As shown in FIG. 9, after 2D/3D registration, bony information in the form of a digitally reconstructed radiograph (DRR) from the CT scan (FIG. 9(a)) can be subtracted from the fluoroscopy image (FIG. 9(b)) to give a "deboned" image (FIG. 9(c)). Note how only the bone is removed leaving the interventional instruments and soft tissue details. As mentioned previously, this deboning process is carried out on each fluoroscopy image to greatly reduce clutter from high contrast bony features. Where the clutter reduction is performed in combination with the tomosynthesis technique described above i.e. where any desired reconstruction image plane can be obtained, then it is usually performed prior to the image reconstruction process i.e. before the back projection from the target image plane and the forward projection into the fluoroscopy images. That is, the clutter reduction is performed separately on each fluoroscopy image after 2D to 3D image registration has been performed, but before the DTS procedure is used to generate the desired reconstruction image plane.

Figure 8:
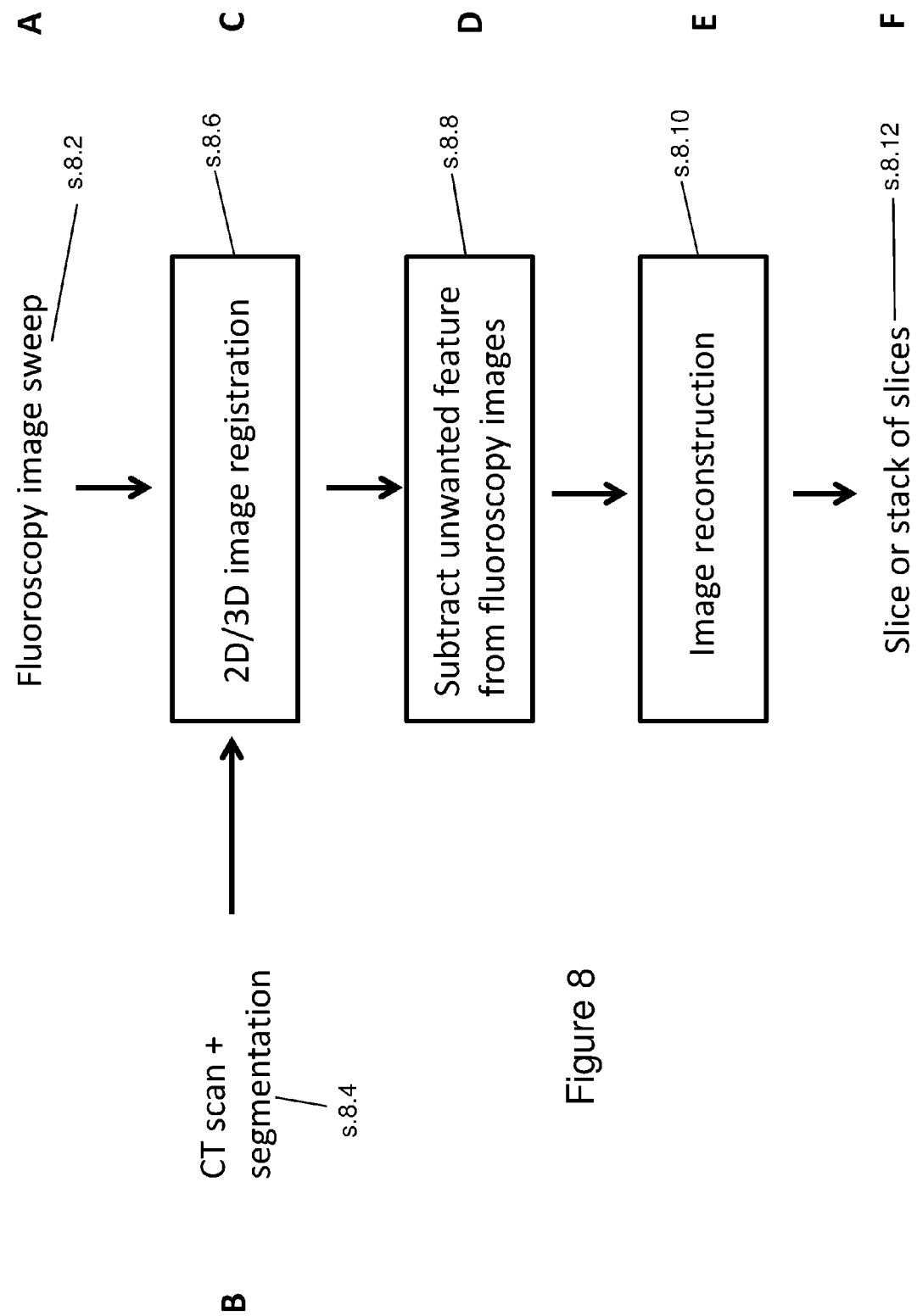
FIG. 8 is a flow diagram of another embodiment of the invention.

FIG. 8 shows the clutter reduction process in more detail. Firstly, at s.8.2 (A) a set of intraoperative fluoroscopy images (9046) from a range of views e.g. sweep from 20 deg RAO to 20 deg LAO are received. Then, similarly at s.8.4 (B) a preoperative CT scan which includes segmentation of unwanted features (i.e. regions defined within the image) which will be removed prior to reconstruction is received (see 3D CT data 9042 in FIG. 14). In the present example embodiment the unwanted features are the vertebrae as we wish to observe the aorta which from an anterior-posterior view is usually a few cm in front of the vertebrae. The vertebrae are high contrast features in a fluoroscopy view and so generate significant out-of-plane artefacts in standard tomosynthesis.

Once the fluoroscopy images 9046 and the 3D imaging data 9042 have been received, at s.8.6 (C) the preoperative CT scan data is registered to each of the fluoroscopy images using 2D-3D image registration, as previously described. For best results the unwanted features should be matched as accurately as possible. In the present example embodiment separate registrations are carried out to each vertebra in the field of view.

Once 2D to 3D registration of each fluoroscopy image has occurred, at s.8.8 (D) unwanted clutter features are subtracted from the fluoroscopy images. In this respect, in this example a digitally reconstructed radiograph (DRR) is produced for each vertebra at the registration position. The DRR image intensities are subtracted from the fluoroscopy image intensities using a weighting function. The weighting function could be determined by minimising the variance in a difference image between the DRR and fluoroscopy. Examples of this procedure are provided in Sections 5.2.2 and 5.2.5 and FIG. 5.1 in "Registration of Tomographic Images to X-ray Projections for Use in Image Guided Interventions" G. Penney, PhD thesis, 2000.

Regarding how the DRRs are obtained, digitally reconstructed radiographs (DRRs) can be produced by casting rays through a CT volume. Each of these rays will go through a number of voxels. If the Hounsfield numbers of these voxels are integrated along the ray and projected onto an imaging plane then the resultant image will resemble a radiograph. Another technique to produce DRRs is known as "wobbled splatting", as described by Birkfellner W et al in *Wobbled splatting—a fast perspective volume rendering method for simulation of x-ray images from CT* Phys Med Biol. 2005 May 7; 50(9):N73-84. Epub 2005 Apr. 13. Any known method of producing DRRs may be used in an embodiment of the invention.

At s.8.10 (E), once the unwanted clutter features have been removed, an output image is reconstructed from the fluoroscopy images from which the unwanted features have been removed. In embodiments of the invention this output image is produced using the DTS method previously described. The output image can either be a single slice, or multiple slices which can be stacked to produce a 3D volume (s.8.12).

Figure 15:
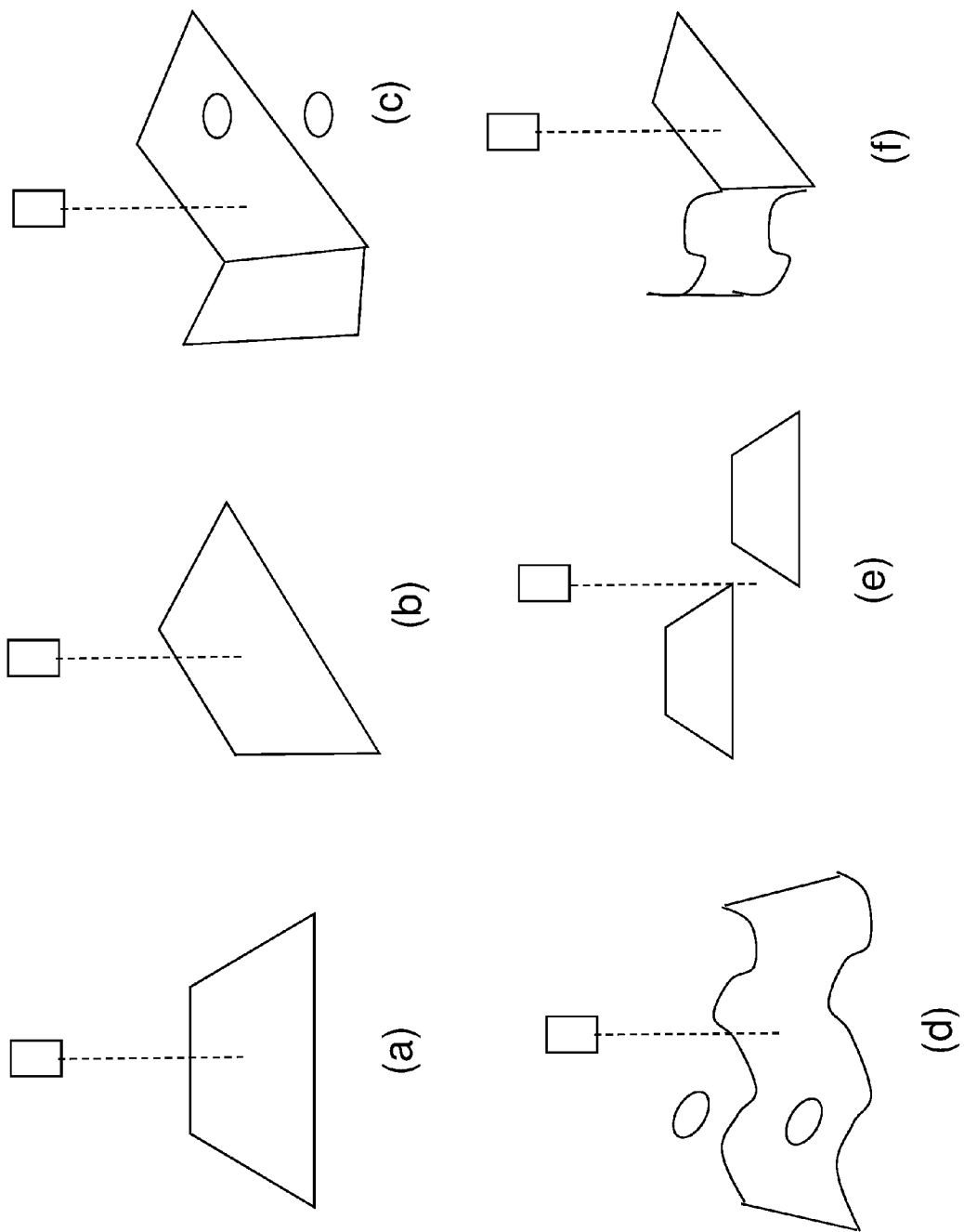
FIG. 15 gives, in (b) to (e) examples imaging planes that may be imaged in embodiments of the invention.

FIG. 15 illustrates some examples of the sort of image generation or reconstruction planes that can be defined in embodiments of the invention. In this respect, FIG. 15(a) shows the conventional tomosynthesis imaging plane, which is typically horizontally oriented, or more precisely usually normal to the imaging axis (shown as a dotted line) of the imaging sensor (such as a fluoroscopy head) when in a central position over the object. Embodiments of the invention, however, allow for different imaging planes to be defined. For example, at its simplest an angled imaging plane can be defined, as shown in FIG. 15(b). FIG. 15(c) shows a discontinuous imaging plane, formed from two angle planes that intersect. In addition, one of the planes has a spatial discontinuity in it, to allow imaging within the discontinuity to be obtained from a different imaging depth, as shown. In this respect, it will be noted that the discontinuous plane at the lower depth is non-overlapping with the main angled plane. FIG. 15(d) shows how a curved image generation plane may be defined, which again, in this example, has a spatial discontinuity in it, so that imaging in the spatial discontinuity is formed at a height above the remainder of the curved plane. FIG. 15(e) is an interesting case, as it shows that two substantially horizontal non-overlapping imaging planes may be defined, but at different depths in the object. Finally, FIG. 15(f) gives an example of how the above may be combined, for example by having a curved imaging plane intersecting with an angled plane to give the whole imaging plane.

It should further be noted that choice of shape of imaging plane between the various examples in FIGS. 15(b) to (f) (which are presented purely by way of example—any other combination and/or configuration of imaging plane within the 3D imaging data set can be defined) is undertaken to highlight specific features, such as, in the clinical context, clinically relevant anatomy, in the 3D data set. In contrast, reconstruction planes in the prior art are usually defined relative to the coordinate system of the imaging device, and hence are agnostic to the actual features being imaged.

With such flexibility in the definition of the image generation or reconstruction plane, therefore, it can be seen that imaging planes can be defined which should allow planar visualisation as a single image of substantially any desired plane, continuous or discontinuous, through the object. Moreover, in the clinical anatomical imaging context, the desired imaging plane is usually defined with reference to a 3D imaging data set of the subject, such that particular anatomical features can be selected to appear in the desired imaging plane.

Various data and results of experiments performed using the above noted embodiments will now be described with respect to FIGS. 10 to 13.

Experiments were carried out using data from an abdominal spine phantom and from two patients who underwent endovascular aortic repair. Data use was approved by national research ethics committee (09/H0707/64) with informed patient consent. Each data set had a preoperative CT scan and an intraoperative fluoroscopy sequence of low dose screening images acquired by rotating the C arm ~20° RAO/LAO with a frame rate of 30 fps, which were resampled to obtain one image per degree of rotation, i.e. ~40 images. For comparison a series of ~40 screening images from an AP view were also saved, and averaged to produce a high contrast image (CI) from a single view direction.

The phantom CT had voxel sizes of 1.094×1.094×1.487 mm3. Prior to fluoroscopy acquisition, an interventional instrument (a catheter) and three bits of Blu-Tack (to represent calcium in the aortic wall) were placed on the anterior surface of the phantom. The anterior surface of the CT volume was segmented and used as a reconstruction surface.

Each clinical data set had a standard diagnostic preoperative CT scan (approximate voxel sizes 0.75×0.75×0.8 mm3) and an intraoperative fluoroscopy sequence. The reconstruction surface was defined to intersect the curved aortic centreline and to be perpendicular to the sagittal plane. This surface was chosen to enhance features of interest such as the aortic walls.

DTS slice reconstruction, as described above, was carried out for all data sets to reconstruct two interventional DTS slices, the first using the standard fluoroscopy images, and the second using the fluoroscopy images after applying the deboning process.

For each data set we show: the target image (TI), the high contrast image (CI), the reconstructed slice (DTS) and the reconstructed slice after deboning, i.e. deboned DTS (DDTS). For the clinical data sets we also show two overlays from the CT scan. The first shows the aorta, and the second shows aortic calcification. The aim of these overlays is to provide context to the features visible in the DTS reconstructed slices.

Figures 12, 13:
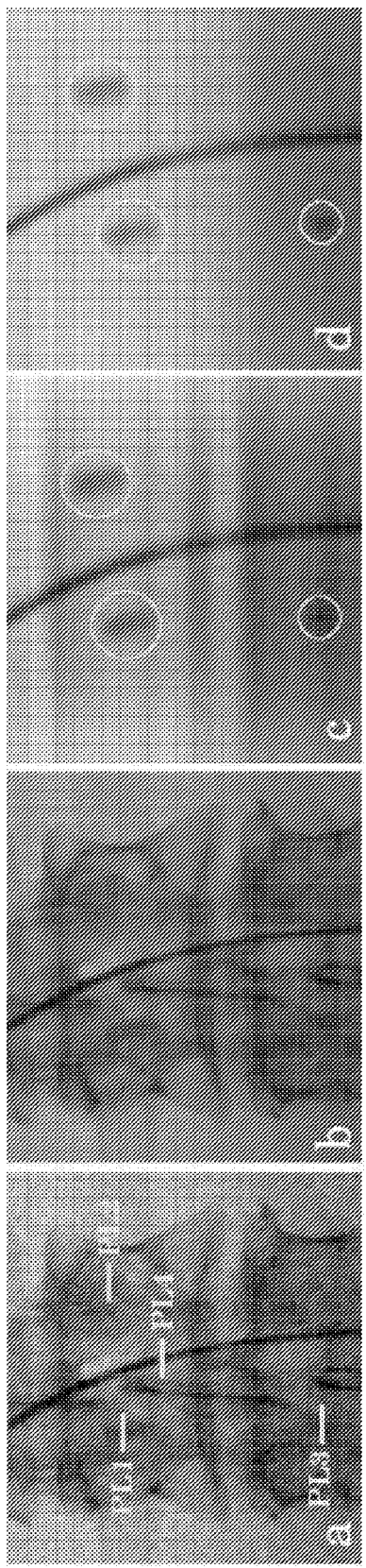
FIG. 12 (a) to (d) are example images produced at various stages by embodiments of the invention.
FIG. 13 is a table of results obtained by embodiments of the invention.

FIG. 12 shows the phantom results. The high contrast catheter can be clearly seen in all images; whereas the low contrast synthetic calcium cannot be clearly distinguished in 'a' or 'b' from the overlying vertebrae. However, in both DTS re-constructions, 'c' and 'd' the synthetic calcium is successfully brought into focus (indicated by circles). Significantly more clutter from the underlying vertebrae can be seen in 'c', compared to the reconstruction after deboning 'd'.

The table in FIG. 13 shows contrast-to-noise ratios (CNR), and percentage improvement in CNR compared to the target image, calculated on the profile lines (PL) shown in FIG. 12. PLs 1, 2 and 3 are through synthetic calcium and PL4 is through the catheter. An average improvement of 72% is seen between TI and CI as random noise is averaged. Similar CNR results are achieved between CI and DDTS for the high contrast catheter. The DTS methods both show much improved CNR compared to TI and CI for the lower contrast synthetic calcium, and the further improvement due to the deboning method is clearly seen.

Figure 10:
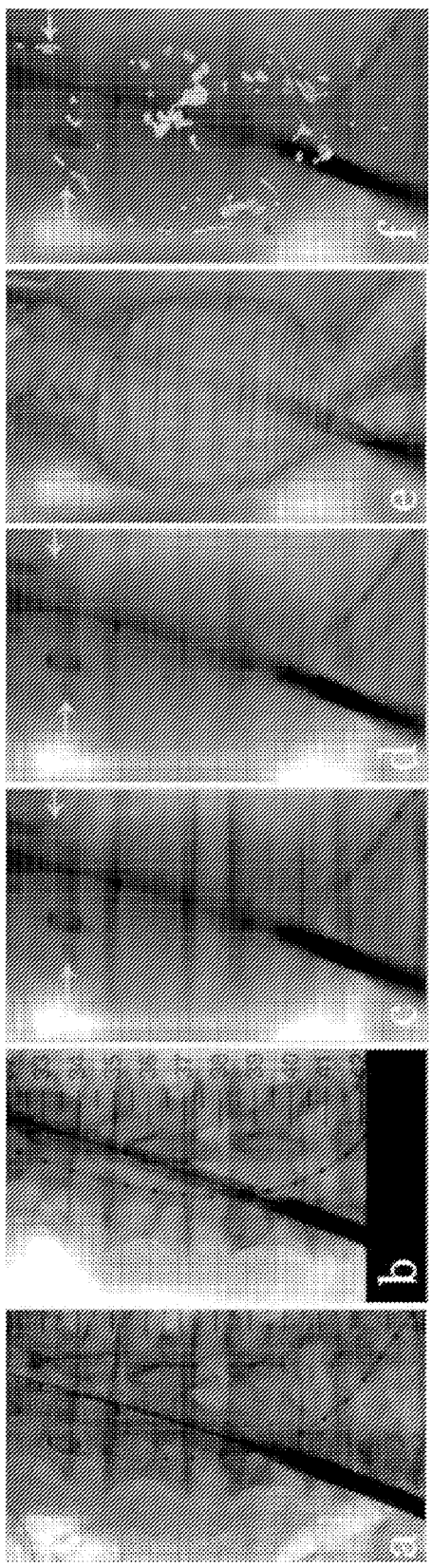
FIGS. 10 and 11 are example results sets obtained by embodiments of the invention.
Figure 11:
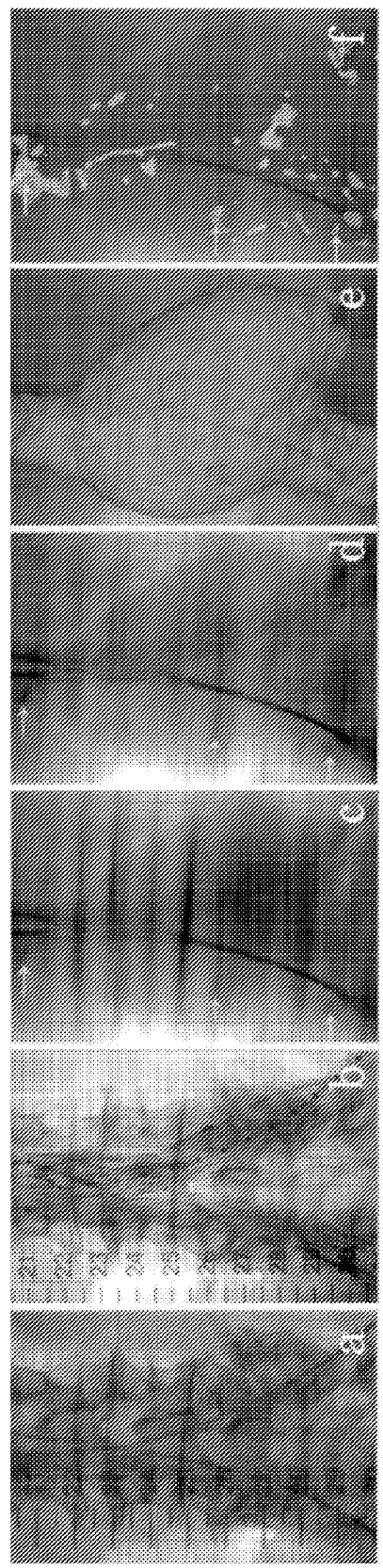

FIGS. 10 and 11 show the patient data results. Comparing the overlay outline in 'e' and 'd' shows how the DDTS method has been able to show the outline of the aorta. Some calcium deposits (indicated by arrows) were also enhanced, and for Patient 1 (shown in FIG. 10) the aortic bifurcation was visible. Comparisons between 'c' and 'd' clearly shows the benefits of the deboning process, and although 'b' shows a high contrast image of the instruments and bony anatomy, none of the clinically relevant soft tissue features enhanced by the DTS process are visible.

In conclusion, the development of novel imaging technologies capable of near-real-time visualization of soft-tissue structures in the interventional suite is challenging. Short acquisition and reconstruction times, low radiation dose and minimal interruption to the clinical work-flow are key requirements for an effective interventional modality. However, embodiments of the invention described herein provide "interventional digital tomosynthesis" techniques which can be directly implemented on existing fluoroscopy systems. The small C-arm sweep of ±20° used in particular embodiments takes a fraction of the image acquisition time and radiation dose compared to CBCT, and causes very little disruption to the clinical workflow.

Embodiments of the invention are also able to enhance clinically important structures situated on a curved surface. These structures could provide additional spatial information during intervention, offering surgeons an increased guidance precision and confidence. For example, visualisation of the aorta would usually require injection of iodinated contrast; thus, contrast usage could potentially be reduced.

The preoperative CT overlays (FIGS. 10 and 11 (*e*) and (*f*)) needed manual adjustment to accurately match our DDTS images. This was due to anatomical deformation occurring during intervention caused by the stiff interventional instruments [8]. This shows a potential application for our interventional DTS: to provide additional information to update overlays from an image guided surgery system enabling more accurate representation of the intraoperative scene.

In overall conclusion therefore embodiments providing interventional DTS are presented. The embodiments employ a 2D/3D registration algorithm to enable production of DTS slices using standard interventional equipment, with much reduced out-of-plane clutter and on a patient tailored reconstruction surface. Preliminary results from a phantom and two patients show the method's ability to automatically enhance structures of clinical interest.

In other embodiments, however, 2D/3D registration may not be required. This will be particularly the case where the subject or object to be imaged can be positioned accurately and reliably in the same relative position with respect to the imaging devices for capture of both the 2D and 3D data sets. This can be achieved in the medical intra-operative environment when a 3D rotational fluoroscopy image (cone-beam CT) can be registered to subsequent 2D fluoroscopy images using mechanical tracking. In other embodiments that fall within the appended claims effective auto-registration between the 2D and 3D images can be achieved simply by accurate positioning of the object for both 2D and 3D image capture, in that provided the object is positioned in exactly the same relative position with respect to the respective 2D and 3D imaging equipment (and specifically with respect to the imaging sensor thereof) a degree of auto registration between the respective sets of 2D and 3D imaging data will be automatically obtained. For example, in some manufacturing or fault inspection applications such accurate and repeatable positioning may be obtained. As such, it should be understood that the 2D to 3D registration step, whilst important for the specific medical related embodiments, is not essential to every embodiment.

In addition, in other embodiments, it may not be necessary at all to obtain any 3D image data set from a 3D imaging process. This would be the case where accurate three dimensional plans or schema of the object to be imaged were already available, for example in the case of a manufactured object. Or in the medical field if a generic anatomical atlas was available which could be tailored by some process (registration for example) to the anatomy of a specific patient. In such cases the desired imaging plane for the 2D images can be defined with respect to the existing 3D plans or schema, and provided accurate and known positioning of the object with respect to the 2D imaging system can be obtained, such that the fixed 3D plans or schema can simply be overlaid thereon then no registration process to the 3D plans or schema would be required. For example, complicated pipework within an object such as an aircraft wing may be imaged for inspection or repair by defining the 2D imaging plane within 3D plans or schema, such as 3D CAD plans of the subject such that the 2D imaging plane follows the pipework.

In addition, whilst we have described the embodiments of the invention in the context of the intra-operative environment in which it was developed, it will be understood that generating images at any desired plane through an object via tomosynthesis may be used in other fields as well, for example manufacturing, product inspection, fault diagnosis, to name a few. Embodiments of the invention are therefore not limited to the specific medical application described above in the specific embodiment.

Various modifications, whether by way of addition, deletion or substitution may be made to the above described embodiment to provide further embodiments, any and all of which are intended to be encompassed by the appended claims.

REFERENCES

1. Bachar, G., Barker, E., Nithiananthan, S., Chan, H., Daly, M., Irish, J., Siewerdsen, J.: Three-dimensional tomosynthesis and cone-beam computed tomography: An experimental study for fast, low-dose intraoperative imaging technology for guidance of sinus and skull base surgery. The Laryngoscope 119(3), 434-441 (2009)
2. Bachar, G., Siewerdsen, J., Daly, M., Jaffray, D., Irish, J.: Image quality and localization accuracy in C-arm tomosynthesis-guided head and neck surgery. Med Phys 34, 4664 (2007)
3. Dobbins, J., McAdams, H.: Chest Tomosynthesis: Technical Principles and Clinical Update. Eur J Radiol 72(2), 244-251 (2009)
4. Dobbins III, J.: Tomosynthesis Imaging: at a Translational Crossroads. Med Phys 36(6), 1956-1967 (2009)
5. Dobbins III, J., Godfrey, D.: Digital x-ray Tomosynthesis: Current State of The Art and Clinical Potential. Phys Med Biol 48(19), 65-106 (2003)
6. Gang, G., Tward, D., Lee, J., Siewerdsen, J.: Anatomical Background and Generalized Detectability in Tomosynthesis and Cone-Beam CT. Med Phys 37(5) (2010)
7. Jaffray, D., Siewerdsen, J., Wong, J., Martinez, A., et al.: Flat-panel cone-beam computed tomography for image-guided radiation therapy. Int J Radiat Oncol Biol Phys 53(5), 1337-1349 (2002)
8. Penney, G., Varnavas, A., Dastur, N., Carrell, T.: An Image-Guided Surgery System to Aid Endovascular Treatment of ComplexAortic Aneurysms: Description and Initial Clinical Experience. In: IPCAI, vol. 6689, pp. 13-24 (2011)
9. Siewerdsen, J., Daly, M., Bachar, G., Moseley, D., Bootsma, G., Brock, K., Ansell, S., Wilson, G., Chhabra, S., Jaffray, D., et al.: Multimode C-arm fluoroscopy, tomosynthesis, and cone-beam CT forimage-guided interventions: from proof of principle to patient protocols. In: Medical Imaging. pp. 65101A-65101A. International Society for Optics and Photonics (2007)
10. Tingberg, A.: X-ray Tomosynthesis: a Review of its Use for Breast and Chest Imaging. Radiat Prot Dosim 139(1-3), 100-107 (2010)
11. Wallace, M., Kuo, M., Glaiberman, C., Binkert, C., Orth, R., Soulez, G.: Three-dimensional C-arm cone-beam CT: applications in the interventional suite. J Vasc Intery Radiol 19(6), 799-813 (2008)

The invention claimed is:
1. An image generation method, comprising:
obtaining a plurality of 2D images through an object to be imaged;
obtaining a 3D image data set of the object to be imaged;
registering, if required, the 2D images with the 3D image data set;
processing the plurality of 2D images to remove clutter features therefrom;
defining within the 3D image data set an image reconstruction plane, being the plane of an image to be reconstructed from the plurality of 2D images;

for a pixel in the image reconstruction plane, mapping corresponding pixel values from the plurality of 2D images thereto, and combining the mapped pixel values into a single value to give a value for the pixel in the image reconstruction plane, wherein the clutter removal comprises, for a 2D image:
obtaining, from the 3D data set, a synthetic image of the clutter to be removed; and
subtracting the synthetic image from the 2D image to give a clutter free 2D image.

2. The method according to claim 1, wherein the image reconstruction plane is any of:
i) angled planar or multi-planar;
ii) curved; and/or
iii) discontinuous;
or any combinations thereof.

3. The method according to claim 1, wherein the image reconstruction plane is shaped to substantially follow a feature in the object to be imaged.

4. The method according to claim 1, wherein the mapping comprises:
defining a target output image plane;
for a pixel in the target output image plane, back projecting from the pixel to the image reconstruction plane, to determine a reconstruction plane interception position;
from the reconstruction plane interception position, forward projecting to the plurality of 2D images to determine respective 2D image interception positions; and
determining a value for the pixel in the target output image plane by combining the values of the pixels at the respective 2D interception positions, preferably wherein the combining is an averaging operation.

5. The method according to claim 1, wherein clutter removal is performed prior to the mapping of pixel values from the 2D images to the image reconstruction plane.

6. The method according to claim 1, wherein, the 3D image data set is obtained from a computerised tomography (CT) or magnetic resonance (MR) or cone beam computerised tomography scan, and the synthetic image is a digitally reconstructed radiograph (DRR).

7. An image generation method, comprising:
obtaining a plurality of 2D images through an object to be imaged;
obtaining a 3D image data set of the object to be imaged;
registering, if required, the 2D images with the 3D image data set;
the method further comprising processing the plurality of 2D images to remove clutter features therefrom, the clutter features being defined in dependence on the 3D image data set,
wherein the clutter removal comprises, for a 2D image:
obtaining a synthetic image of the clutter to be removed from the 3D data set; and
subtracting the synthetic image from the 2D image to give a clutter free 2D image.

8. The method according to claim 7, and further comprising generating digital tomosynthesis (DTS) image slices from the plurality of 2D images, wherein clutter removal is performed prior to the generation of the DTS image slices.

9. The method according to claim 7, wherein, the 3D image data set is obtained from a computerised tomography (CT) or magnetic resonance (MR) or cone beam computerised tomography scan, and the synthetic image is a digitally reconstructed radiograph (DRR).

10. The method according to claim 7, wherein the 2D images are fluoroscopy images.

11. The method according to claim 7, wherein the 3D image data set is a CT or MR or cone beam CT data set.

12. The method according to claim 7, wherein the method is an intraoperative method used during a surgical procedure on the human or animal body.

13. An image generation system, comprising:
an image processor, the image processor being arranged to:
register, if required, a plurality of 2D images through an object to be imaged with a 3D image data set of the object to be imaged;
define an image reconstruction plane using the 3D image data set, being the plane of an image to be reconstructed from the plurality of 2D images;
for a pixel in the image reconstruction plane, map corresponding pixel values from the plurality of 2D images thereto, and combine the mapped pixel values into a single value to give a value for the pixel in the image reconstruction plane,
wherein the image processor is further arranged to process the plurality of 2D images to remove clutter features therefrom,
wherein the clutter removal comprises, for a 2D image:
obtaining a synthetic image of the clutter to be removed from the 3D data set; and
subtracting the synthetic image from the 2D image to give a clutter free 2D image.

14. The system according to claim 13, wherein the image reconstruction plane is any of:
i) angled planar or multi-planar;
ii) curved; and/or
iii) discontinuous;
or any combinations thereof.

15. The system according to claim 13, wherein the image reconstruction plane is shaped to substantially follow a feature in the object to be imaged.

16. The system according to claim 13, wherein the mapping comprises:
defining a target output image plane;
for a pixel in the target output image plane, back projecting from the pixel to the image reconstruction plane, to determine a reconstruction plane interception position;
from the reconstruction plane interception position, forward projecting to the plurality of 2D images to determine respective 2D image interception positions; and
determining a value for the pixel in the target output image plane by combining the values of the pixels at the respective 2D interception positions, preferably wherein the combining is an averaging operation.

17. The system according to claim 13, wherein clutter removal is performed prior to the mapping of pixel values from the 2D images to the image reconstruction plane.

18. The system according to claim 13, wherein, the 3D image data set is obtained from a computerised tomography (CT) or magnetic resonance (MR) or cone beam computerised tomography scan, and the synthetic image is a digitally reconstructed radiograph (DRR).

* * * * *